United States Patent [19]

Hoover et al.

[11] 3,976,641

[45] Aug. 24, 1976

[54] CEPHALOSPORIN INTERMEDIATES AND PROCESS THEREFOR

[75] Inventors: John R. E. Hoover, Glenside; Timothy Yu-Wen Jen, Broomall, both of Pa.

[73] Assignee: SmithKline Corporation, Philadelphia, Pa.

[22] Filed: Nov. 14, 1974

[21] Appl. No.: 523,769

Related U.S. Application Data

[63] Continuation-in-part of Ser. No. 414,008, Nov. 8, 1973, abandoned.

[52] U.S. Cl. ............................ 260/243 R; 424/246
[51] Int. Cl.[2] ...................................... C07D 279/08
[58] Field of Search ............................... 260/243 R

[56] References Cited
UNITED STATES PATENTS 3,875,151   4/1975   Fechtig et al. ................... 260/243
3,893,997   7/1975   Cooper et al. ................... 260/210

OTHER PUBLICATIONS

McOmie (Ed.) "Protective Groups in Organic Chemistry, " Chapter 5, pp. 183–215, Plenum Press, London & New York, (1973).

B425,470, Jan. 1975, Rapoport, 260/243.

*Primary Examiner*—John M. Ford
*Attorney, Agent, or Firm*—Stuart R. Suter; Alan D. Lourie; William H. Edgerton

[57] ABSTRACT

Novel 7-oxocephalosporins and a process for preparing them are disclosed. These compounds are useful intermediates in the preparation of other cephalosporins which have antibacterial activity.

9 Claims, No Drawings

CEPHALOSPORIN INTERMEDIATES AND PROCESS THEREFOR

This application is a continuation-in-part of copending application Ser. No. 414,008, filed Nov. 8, 1973, now abandoned.

This invention relates to cephalosporin compounds which are useful intermediates in the preparation of novel cephalosporins with antibacterial activity and to processes for preparing these intermediates. In particular the compounds of this invention contain a 7-oxo group.

The compounds of this invention are more fully defined by the following structural formula

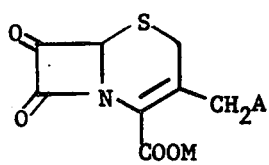

wherein
A is any noninterfering group and
M is hydrogen or a protecting ester group.

Noninterfering groups are those which do not interfere in the conversion of a 7-amino-7-methylthio compound to the 7-oxo compound and in the subsequent Wittig reaction. They include hydrogen, alkoxy of 1–4 carbons, alkylthio of 1–4 carbons, alkanoyloxy of 2–8 carbons, and S-Het where Het is tetrazolyl, thiadiazolyl, oxadiazolyl, triazolyl, diazolyl, pyridyl, pyrimidyl, pyrazinyl or similar heterocyclic group. The heterocyclic group may be unsubstituted or substituted with one or two lower alkyl groups of up to 6 carbon atoms each.

The protecting ester group is any easily removable group which is used to protect carboxylic acids in the cephalosporin or peptide synthesis arts. Examples of such groups include t-butyl, benzyl, benzhydryl, 2,2,2-trichloroethyl, benzyloxymethyl, p-nitrophenyl, p-methoxyphenyl, p-methoxybenzyl, p-nitrobenzyl and the like. The choice of the ester group is not critical and is within the ability of one skilled in the art.

The compounds of this invention are prepared by a sequence of reactions outlined below from 7-aminocephalosporins which are themselves known or prepared by standard procedures well known in the art.

The 7-aminocephalosporanic acid ester (I) is converted to the 7β-amino-7α-methylthio derivative (II) by condensing the amine with an aldehyde, for example, benzaldehyde, and then reacting the resulting Schiff base with a base strong enough to remove the α-hydrogen, for example, sodium hydride, and then with methyl methanethiosulfonate. Hydrolysis of the Schiff base moiety by standard methods, such as aqueous hydrochloric or sulfuric acids, gives compound II. The 7β-amino-7α-methylthio compound (II) is converted into the desired 7-oxocephalosporanic acid ester by either of two methods. The preferred method is stirring compound II in a water misible organic solvent which will dissolve the cephalosporin and the metal salt, for example, dimethylformamide, acetonitrile, dioxane, or dimethylsulfoxide, with a small amount of water in the presence of metal salts which will coordinate with the sulfur and assist in the breaking of the carbon-sulfur bond. Examples of such metals are mercury and silver salts such as mercuric chloride and silver chloride. Alternatively, the 7-oxocephalosporin is obtained by refluxing a mineral acid salt, such as hydrochloride, sulfate, or nitrate, of II in wet methanol or a similar organic solvent such as acetone, tetrahydrofuran, or dimethylformamide, containing water sufficient to effect the desired reaction.

The 7-oxocephalosporin may sometimes be isolated from the reaction mixture as its hydrate; however, this is easily converted to the desired ketone by drying in vacuo at 25° to 60°.

The new 7-oxocephalosporins are useful intermediates in the preparation of novel cephalosporins. For example, treatment of 7-oxocephalosporanic acid esters with a phenoxyacetylmethylenetriphenylphosphorane gives 7-phenoxyacetylmethylenecephalosporanic acid esters. Catalytic hydrogenation of the methylene double bond with Pt, Pd or like catalysis followed by cleavage of any ester protecting group gives 7β-phenoxyacetylmethylcephalosporins which are antibacterial agents. Many novel cephalosporins can be prepared by using various acylmethylenetriphenylphoranes, the preparation and reaction of which is within the ability of one skilled in the art.

In addition, reduction of the 7-oxocephalosporins gives 7-hydroxycephalosporins which can be acylated with various acyl groups known in the cephalosporin art. For example, acylation of t-butyl 7-hydroxycephalosporanate with phenoxyacetyl chloride gives, after removal of the protecting ester, 7-phenoxyacetoxycephalosporanic acid. This compound exhibits anti-

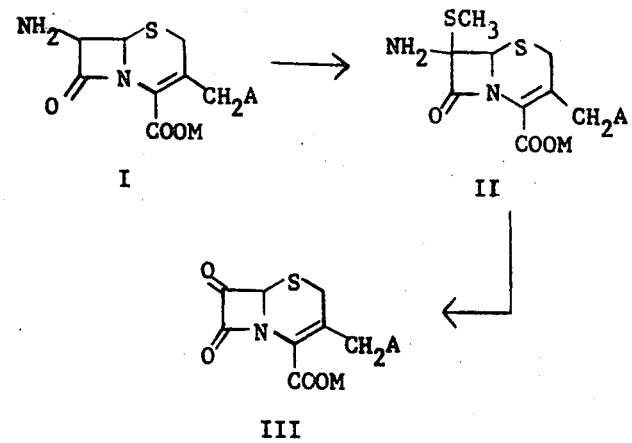

I  II

III bacterial activity against a variety of Gram-positive and Gram-negative bacteria.

The following Preparations illustrate the preparation of the starting materials and the following Examples illustrate the processes and products of this invention. They are not intended to be limitative of the scope of the invention.

PREPARATION 1 t-Butyl 7β-amino-7α-methylthiodeacetoxycephalosporanate

A solution of t-butyl deacetoxycephalosporanate (54 g, 0.2 mol) in methanol (500 ml) was treated with benzaldehyde (23 g, 0.22 mol). After chilling the mixture, the crystalline product was filtered, washed with a small amount of cold methanol, and dried to give t-butyl 7β-benzlideneaminodeacetoxycephalosporanate.

To a stirred solution of t-butyl 7β-benzylideneaminodeacetoxycephalosporanate (2.16 g, 6.0 mmol) in anhydrous DMF (60 ml) at −15°C under nitrogen was added sodium hydride (6.3 mmol). After 40 minutes, methyl methanethiosulfonate (0.755 g, 6.0 mmoles) was added and stirring was continued for 10 minutes. The mixture was then diluted with ether (150 ml), washed thoroughly with water, once with 5% sodium bicarbonate solution, and dried over calcium sulfate. Evaporation of the solvent and recrystallization of the residue from acetone-hexane gave 1.45 g of the 7α-methylthio derivative, mp 161°–162°C.

A solution of t-butyl 7β-benzlideneamino-7α-methylthiodeacetoxycephalosporanate (13.9 g, 34.4 mmol) in 150 ml of acetone was treated with a solution of 12N hydrochloric acid (3 ml, 36 mmol) in 1.5 ml of water. When crystallization occurred, the mixture was diluted with ether (200 ml), chilled, and filtered to give 11.0 g of the hydrochloride salt of the title product, mp 130°–135°C.

The free base of the titled product (mp 169°–171°C) was obtained quantitatively by treatment of the hydrochloride salt with 5% sodium bicarbonate solution and extraction of the product into methylene chloride.

PREPARATION 2 t-Butyl 7β-amino-7α-methylthiocephalosporanate t-Butyl 7β-aminocephalosporanate (3.28 g, 10 mmol) and benzaldehyde (1.28 g, 10.5 mmol) in methanol (250 ml) are stirred at 25°C for 30 minutes and warmed on steam bath for 10 minutes. The solvent is evaporated and the moisture is removed by repeated azeotropic distillation with benzene to give t-butyl 7β-benzylideneaminocephalosporanate.

The above product (3.2 g, 7.9 mmol) in anhydrous dimethylformamide (80 ml) is treated with sodium hydride (8.3 mmol) and methyl methanethiosulfonate (7.9 mmol) in the same manner described in Preparation 1. Following similar work-up procedures, the 7α-methylthio compound is obtained.

t-Butyl 7β-benzylideneamino-7α-methylthiocephalosporanate in acetone is treated with a slight excess of hydrochloric acid in the same manner described in Preparation 1 to give the hydrochloride salt of the title product which is converted to the free base by treatment with 5% sodium bicarbonate solution and extraction with methylene chloride.

EXAMPLE 1 t-Butyl 7-oxodeacetoxycephalosporanate

METHOD A

To a stirred solution of t-butyl 7β-amino-7α-methylthiodeacetoxycephalosporanate (4.0 g, 12.66 mmol) in a mixture of dimethylformamide (75 ml) and water (2.5 ml) was added HgCl$_2$ (3.43 g, 12.66 mmol). After stirring at 25° for 30 minutes, ether (300 ml) and water (300 ml) were added. The mixture was filtered, the ether was separated and the aqueous phase extracted with fresh ether (150 ml). The combined ether solutions were washed with water, dried and evaporated to an oil which was passed rapidly through a Florisil column using ether as eluant. The title product (1.8 g) was obtained as a yellow oil.

METHOD B

A solution of t-butyl 7β-amino-7α-methylthiodeacetoxycephalosporanate hydrochloride (30 mg) in wet methanol (2 ml) was refluxed for 1.5 hours. The solvent was evaporated and the resultant residue was extracted with ether and filtered. Evaporation of the ether gave the title compound.

Tetrahydrofuran-water and acetone-water gave similar results. When the above hydrochloride salt was treated with tetrahydrofuran-HCl and dimethylformamide-HCl, the title product was obtained.

EXAMPLE 2 t-Butyl 7-oxocephalosporanate

A solution of t-butyl 7β-amino-7α-methylthiocephalosporanate (4.7 g, 12.66 mmol) in dimethylformamide (75 ml) and water (2.5 ml) is treated with HgCl$_2$ (3.43 g, 12.66 mmol) in the same manner as in Example 1 Method A. Following the same work-up procedures the title compound is obtained.

EXAMPLE 3

7β-Phenoxyacetylmethyldeacetoxycephalosporanic acid

A solution of t-butyl 7-oxodeacetoxycephalosporanate (0.8 g, 3 mmol) and phenoxyacetylmethylenetriphenylphosphorane (1.29 g, 3.1 mmol) in benzene (100 ml) is refluxed for 4 hours. The solvent is evaporated and the residue is chromatographed on a silica gel column. The isolated unsaturated product is dissolved in ethyl acetate and hydrogenated over PtO$_2$ until 1 molar equivalent of hydrogen is taken up. Evaporation of the solvent gives the product slightly contaminated with its trans epimer which is removed by chromatography on silica gel.

The resulting product is treated with trifluoroacetic acid (10 ml) at 10° for 1 hour. The excess trifluoroacetic acid is evaporated and the residue is triturated with ether-hexane to give the title product.

EXAMPLE 4

7β-Phenoxyacetylmethylcephalosporanic acid t-Butyl 7-oxocephalosporanate is reacted with phenoxyacetylmethylenetriphenylphosphorane; the resultant product is hydrogenated over PtO$_2$ and treated with trifluoroacetic acid, all according to the procedure of Example 3, to give the title product.

EXAMPLE 5

When the appropriate 7β-amino-7α-methylthiodeacetoxycephalosporanic acid ester, prepared by a procedure analogous to Preparation 1, is treated with water and HgCl₂ according to the procedure of Example 1, Method A, the following 7-oxo derivatives are obtained.

Benzyl 7-oxodeacetoxycephalosporanate
Benzhydryl 7-oxodeacetoxycephalosporanate
2,2,2-Trichloroethyl 7-oxodeacetoxycephalosporanate
Benzyloxymethyl 7-oxodeacetoxycephalosporanate
p-Nitrophenyl 7-oxodeacetoxycephalosporanate
p-Methoxyphenyl 7-oxodeacetoxycephalosporanate
p-Methoxybenzyl 7-oxodeacetoxycephalosporanate
p-Nitrobenzyl 7-oxodeacetoxycephalosporanate They are used in the same manner as is described in Examples 3 and 8.

EXAMPLE 6

When the appropriate 7β-amino-7α-methylthiocephalosporanic acid ester, prepared by a procedure analogous to Preparation 2, is treated with water and HgCl₂ according to the procedure of Example 2 the following 7-oxo derivatives are obtained.

Benzyl 7-oxocephalosporanate
Benzhydryl 7-oxocephalosporanate
2,2,2-Trichloroethyl 7-oxocephalosporanate
Benzyloxymethyl 7-oxocephalosporanate
p-Nitrophenyl 7-oxocephalosporanate
p-Methoxyphenyl 7-oxocephalosporanate
p-Methoxybenzyl 7-oxocephalosporanate
p-Nitrobenzyl 7-oxocephalosporanate They are used in the same manner as is described in Examples 3 and 8.

EXAMPLE 7

Treatment of other 3-substituted 7β-amino-7α-methylthiocephalosporanic acid esters, which are prepared according to the procedure of Preparation 1, with water and HgCl₂ according to Method A of Example 1 gives the corresponding 3-substituted-7-oxocephalosporanic acid ester. Representative examples include t-butyl 7-oxo-3-methylthiomethyl-3-cephem-4-carboxylate
t-butyl 7-oxo-3-methoxymethyl-3-cephem-4-carboxylate
t-butyl 7-oxo-3-(1-methyltetrazol-5-ylthiomethyl)-3-cephem-4-carboxylate
t-butyl 7-oxo-3-(5-methyl-1,3,4-thiadiazol-2-ylthiomethyl)-3-cephem-4-carboxylate
t-butyl 7-oxo-3-(4-methyl-1,2,4-triazol-3-ylthiomethyl)-3-cephem-4-carboxylate
t-butyl 7-oxo-3-(1-methyl-1,2,3-triazol-5-ylthiomethyl)-3-cephem-4-carboxylate
t-butyl 7-oxo-3-(5-methyl-1,3,4-oxadiazol-2-ylthiomethyl)-3-cephem-4-carboxylate
t-butyl 7-oxo-3-(pyrimid-2-ylthiomethyl)-3-cephem-4-carboxylate
t-butyl 7-oxo-3-(1,2,3-triazol-4-ylthiomethyl)-3-cephem-4-carboxylate.

They are used in the same manner as is described in Examples 3 and 8.

EXAMPLE 8 t-Butyl 7-oxocephalosporanate, in its hydrate form (1.38 g, 4 mmol) is dissolved in isopropanol (75 ml) at 0°. NaBH₄ (150 mg) is added over a 2.5 minute period while the pH is maintained at 7 by the addition of acetic acid. The reaction is stirred an additional 2.5 minutes and then quenched with 10% acetic acid. The solution is reduced to one-third of its volume and diluted with ethyl acetate (100 ml). The resulting solution is extracted with saturated NaCl solution, dried, and evaporated to give t-butyl 7β-hydroxycephalosporanate.

To a solution of the above product (448 mg, 1.35 mmol) in anhydrous ether (60 ml) at 0° is added pyridine (0.1 ml) and then phenoxyacetyl chloride (240 mg, 1.4 mmol). The reaction is stirred at 0° for 1 hour and at room temperature for 0.5 hour and then diluted with ice water. The aqueous phase is separated and reextracted with ether. The combined ether phases are dried and evaporated to give the acylated product.

The above product is treated with trifluoroacetic acid containing 1% anisole for 2 hours at room temperature. The reaction is evaporated in vacuo and the residue is triturated with hexane to give 7β-phenyloxyacetoxycephalosporanic acid.

We claim:
1. A compound of the formula

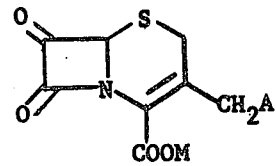

where
A is hydrogen, alkanoyloxy of 2–8 carbons, alkoxy of 1–4 carbons, alkylthio of 1–4 carbons, or SHet;
Het is a member selected from the group consisting of tetrazolyl, thiadiazolyl, oxadiazolyl, triazolyl, diazolyl, pyridyl, pyrimidyl, or pyrazinyl, each Het being unsubstituted or substituted with one or two alkyl groups of 1–6 carbons; and
M is hydrogen or an easily removable protecting ester group.

2. A compound as claimed in claim 1 where M is hydrogen, t-butyl, benzyl, benzhydryl, 2,2,2-trichloroethyl, benzyloxymethyl, p-nitrophenyl, p-methoxyphenyl, p-methoxybenzyl or p-nitrobenzyl.

3. A compound as claimed in claim 2 where A is hydrogen.

4. A compound as claimed in claim 2 where A is acetoxy.

5. A compound as claimed in claim 3 being the compound t-butyl 7-oxodeacetoxycephalosporanate.

6. A compound as claimed in claim 4 being the compound t-butyl 7-oxocephalosporanate.

7. A process for preparing a compound of the formula

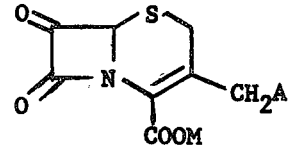

where
A is hydrogen, alkanoyloxy of 2–8 carbons, alkoxy of 1–4 carbons, alkylthio of 1–4 carbons, or SHet;
Het is a member selected from the group consisting of tetrazolyl, thiadiazolyl, oxadiazolyl, triazolyl, diazolyl, pyridyl, pyrimidyl, or pyrazinyl, each said Het being unsubstituted or substituted with one or two alkyl groups of 1–6 carbons, and
M is hydrogen or an easily removable protecting ester group comprising
1. treating an aminomethylthio compound of the formula

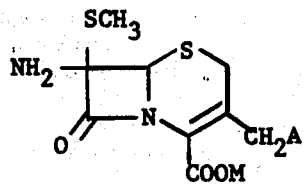

where A and M are as defined above with a water containing water misible organic solvent and a metal complexing salt, or
2. treating a mineral acid salt of said aminomethylthio compound with a water containing water misible organic solvent.

8. A process as claimed in claim 7 where M is hydrogen, t-butyl, benzyl, benzyhydryl, 2,2,2-trichloroethyl, benzyloxymethyl, p-nitrophenyl, p-methoxyphenyl, p-methoxybenzyl, or p-nitrobenzyl.

9. A process as claimed in claim 8 where the complexing salt is a mercuric or silver salt.

* * * * *